(12) United States Patent
Gartner et al.

(10) Patent No.: US 12,263,256 B2
(45) Date of Patent: Apr. 1, 2025

(54) MEDICAL DEVICE TO DISINFECT A SKIN SURFACE

(71) Applicant: Becton, Dickinson and Company, Franklin Lakes, NJ (US)

(72) Inventors: Jeremy Gartner, Closter, NJ (US); Maryann Fam, Secaucus, NJ (US); Peter Girgis, East Brunswick, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 530 days.

(21) Appl. No.: 16/988,576

(22) Filed: Aug. 7, 2020

(65) Prior Publication Data

US 2020/0368375 A1 Nov. 26, 2020

Related U.S. Application Data

(63) Continuation-in-part of application No. 16/777,553, filed on Jan. 30, 2020.

(60) Provisional application No. 62/804,415, filed on Feb. 12, 2019.

(51) Int. Cl.
*A61M 5/32* (2006.01)
*A61L 2/00* (2006.01)
*A61L 2/10* (2006.01)
*A61M 5/42* (2006.01)
*A61L 2/08* (2006.01)

(52) U.S. Cl.
CPC ......... *A61L 2/0047* (2013.01); *A61M 5/3202* (2013.01); *A61M 5/422* (2013.01); *A61L 2/08* (2013.01); *A61L 2202/24* (2013.01)

(58) Field of Classification Search
CPC ............ A61L 2/10; A61L 2/0047; A61L 2/08; A61M 5/3202
See application file for complete search history.

(56) References Cited

U.S. PATENT DOCUMENTS

| | | | |
|---|---|---|---|
| 3,270,743 A | 9/1966 | Gingras | |
| 4,018,222 A | 4/1977 | McAleer | |
| 5,281,198 A * | 1/1994 | Haber | A61J 1/2093 604/209 |

(Continued)

FOREIGN PATENT DOCUMENTS

| CN | 201572389 U | 9/2010 |
|---|---|---|
| CN | 102686253 A | 9/2012 |

(Continued)

OTHER PUBLICATIONS

Mobile Klean, Cleans and Sanitizes iPhones, Macs, and Tablets, made aware of on Apr. 20, 2020, pp. 1-10; https://www.mobileklean.com/.

(Continued)

*Primary Examiner* — Kevin Joyner
(74) *Attorney, Agent, or Firm* — Dickinson Wright, PLLC (57) ABSTRACT

A medical device and method configured to disinfect a skin surface, the device comprising a power source that provides electric power, a light emitting source that uses electric power received from the power source to disinfect the skin surface, and a switch that is configured to be operated by user action, wherein upon activation of the switch, the electric power from the power source is received by the light emitting source to emit visible light and disinfect the skin surface.

25 Claims, 7 Drawing Sheets

(56) References Cited

U.S. PATENT DOCUMENTS

| | | | |
|---|---|---|---|
| 5,405,332 A | 4/1995 | Opalek | |
| 5,863,214 A * | 1/1999 | Hanak | H01R 13/639 |
| | | | 439/352 |
| 5,989,229 A | 11/1999 | Chiappetta | |
| 6,063,040 A | 5/2000 | Owen | |
| 2002/0039068 A1* | 4/2002 | Holowick | G01D 4/008 |
| | | | 340/870.28 |
| 2003/0018373 A1 | 1/2003 | Echardt et al. | |
| 2003/0127506 A1* | 7/2003 | Braun, Jr. | A61L 2/202 |
| | | | 232/31 |
| 2004/0215225 A1 | 10/2004 | Nakayama | |
| 2004/0256581 A1 | 12/2004 | Au et al. | |
| 2006/0001657 A1* | 1/2006 | Monney | G06F 3/03543 |
| | | | 345/184 |
| 2006/0229562 A1 | 10/2006 | Marsh et al. | |
| 2007/0149924 A1 | 6/2007 | Marsh | |
| 2007/0176117 A1 | 8/2007 | Redmond et al. | |
| 2010/0041161 A1* | 2/2010 | Ferrao De Paiva Martins | |
| | | | G01N 21/31 |
| | | | 436/164 |
| 2010/0201274 A1* | 8/2010 | Deixler | H05B 45/22 |
| | | | 315/152 |
| 2012/0029469 A1 | 2/2012 | Horvath et al. | |
| 2012/0217417 A1* | 8/2012 | Schoening | G01N 21/6447 |
| | | | 250/461.1 |
| 2013/0303996 A1* | 11/2013 | Rasooly | A61L 2/10 |
| | | | 604/264 |
| 2013/0323119 A1 | 12/2013 | Alwan | |
| 2013/0323120 A1 | 12/2013 | Ma | |
| 2014/0148784 A1 | 5/2014 | Anderson et al. | |
| 2015/0290347 A1 | 10/2015 | Braden et al. | |
| 2016/0015499 A1 | 1/2016 | Scott | |
| 2016/0199589 A1 | 7/2016 | Plumptre | |
| 2016/0243318 A1 | 8/2016 | Despa et al. | |
| 2016/0375163 A1* | 12/2016 | Hawkins | H05B 47/175 |
| | | | 422/22 |
| 2017/0080117 A1* | 3/2017 | Gordon | A61L 2/084 |
| 2018/0250472 A1 | 9/2018 | Anderson et al. | |
| 2018/0320872 A1* | 11/2018 | Weeks, Jr. | F21V 23/0471 |
| 2019/0374668 A1* | 12/2019 | Kopperschmidt | A01N 59/12 |
| 2020/0254187 A1 | 8/2020 | Fam et al. | |

FOREIGN PATENT DOCUMENTS

| | | |
|---|---|---|
| CN | 103127536 A | 6/2013 |
| CN | 209221354 U | 8/2019 |
| JP | 2005028109 A | 2/2005 |
| KR | 20170019025 A | 2/2017 |
| KR | 20190113497 A | 10/2019 |
| WO | 20180111776 A1 | 12/2017 |
| WO | 2018/013581 A1 | 1/2018 |
| WO | 2018027248 A2 | 2/2018 |
| WO | 2018027248 A3 | 2/2018 |
| WO | 2019087198 A1 | 11/2018 |
| WO | 2019160687 | 8/2019 |
| WO | 20200167486 A1 | 8/2020 |

OTHER PUBLICATIONS

Danielle Kirsch, UVC LEDs: Energizing a new generation of portable, healthcare disinfection devices, Oct. 11, 2017, pp. 1-12; https://www.medicaldesignandoutsourcing.com/.

* cited by examiner

MEDICAL DEVICE TO DISINFECT A SKIN SURFACE

RELATED APPLICATIONS

This application is a continuation-in-part of U.S. Non-provisional application Ser. No. 16/777,553, filed Jan. 30, 2020, which claims the benefit of U.S. Provisional Patent Application Ser. No. 62/804,415, filed on Feb. 12, 2019, which are both hereby incorporated by reference in their entirety.

FIELD OF THE INVENTION

The present invention relates to a medical device that disinfects a skin surface at an injection site prior to administering medicament.

BACKGROUND OF THE INVENTION

Insulin and other injectable medications are commonly given with a medical device, such as a drug delivery device or a medication delivery pen, whereby a disposable pen needle is attached to facilitate drug container access and allow fluid egress from the container, through the needle and into the patient.

As technology and competition advance, driving the desire for shorter, thinner, less painful, and more efficacious injections, the design of the drug delivery devices such as a pen needle and parts thereof becomes more and more important. Designs need to proactively address ergonomically improving injection technique, injection depth control and accuracy, the ability to be safely used and transported for disposal, sterilization, disinfection, and protection against misuse while maintaining the ability to be economically manufactured on a mass production scale.

Figure 1:
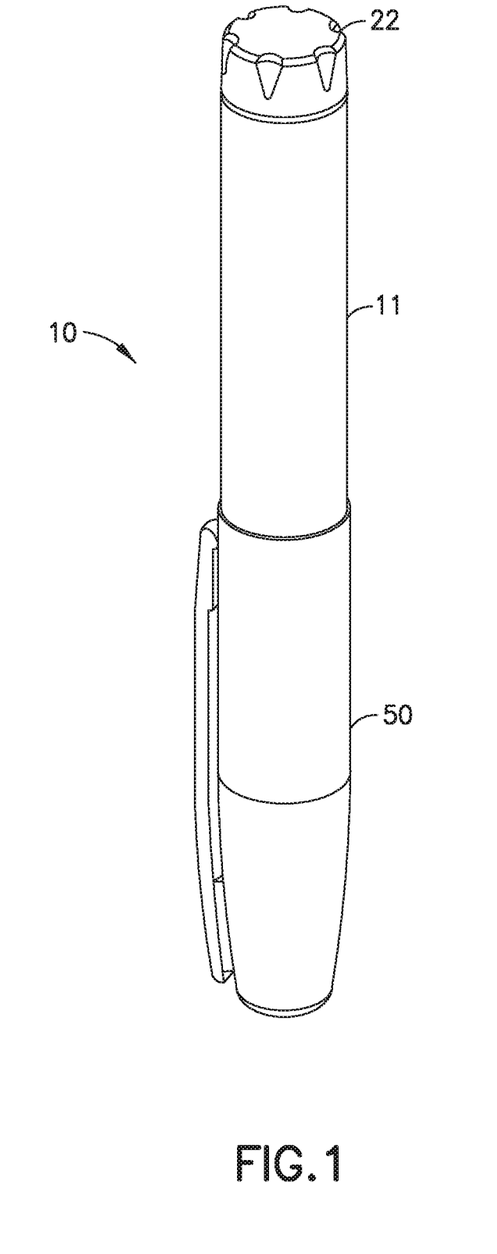
FIG. 1 is a perspective view of an assembled medication delivery pen of the prior art.
Figure 2:
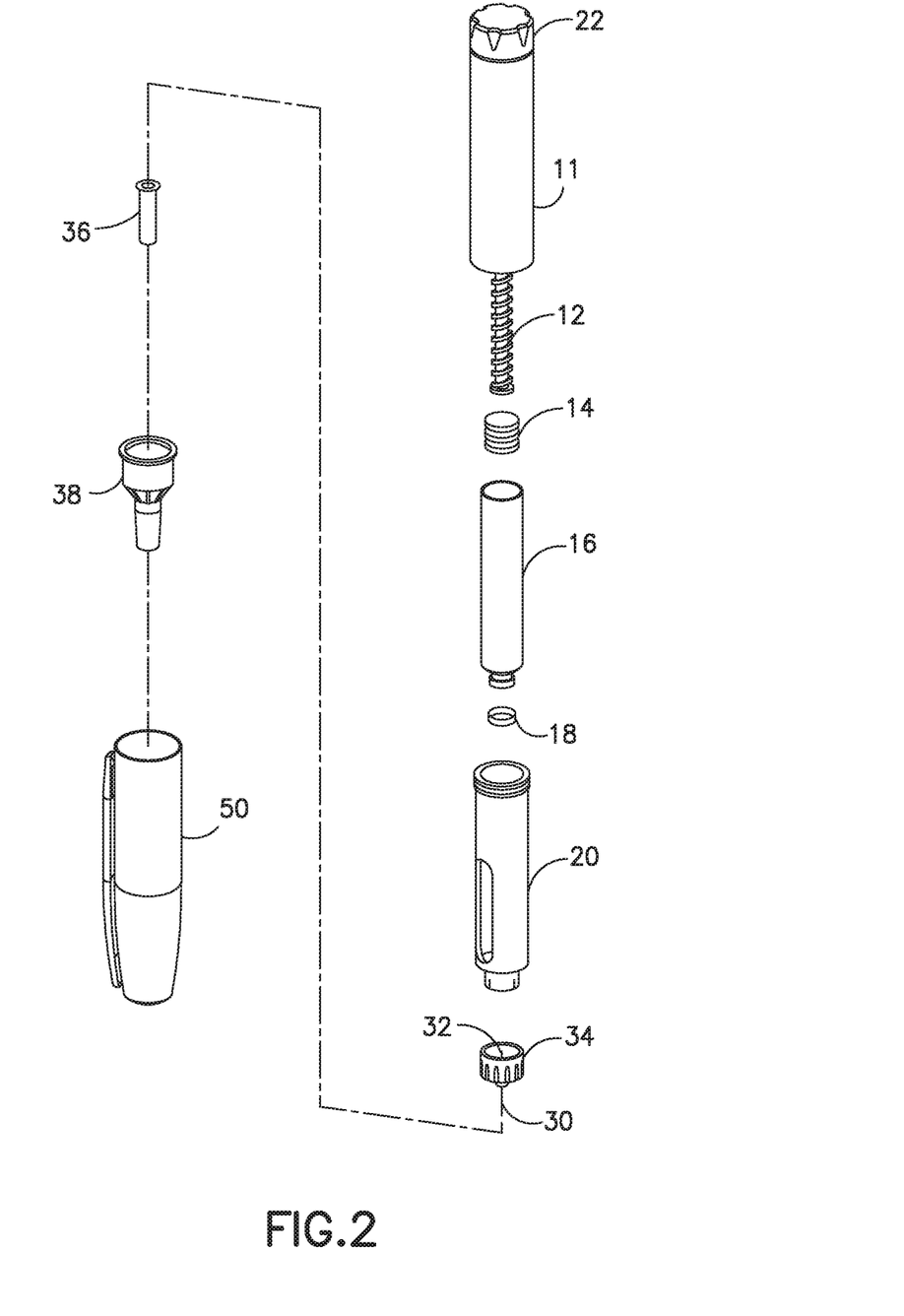
FIG. 2 is an exploded perspective view of the components of the medication delivery pen of FIG. 1 and of a pen needle.

Drug delivery devices, such as the exemplary medication delivery pen 10 shown in FIGS. 1 and 2, can be designed for subcutaneous as well as intradermal injections, and typically comprise a dose knob/button 22, an outer sleeve or housing 11, and a cap 50. The dose knob/button 22 allows a clinician or patient to set the dosage of medication to be injected. The housing 11 is gripped by the user when injecting medication. The cap 50 can be used by the user to securely hold the medication delivery pen 10 in a shirt pocket, purse or other suitable location and provide cover/protection from accidental needle injury. The cap 50 is also used to cover a septum 18 of the medicament cartridge 16 in the medication delivery pen 10 before and after use. Otherwise, the septum 18 would be exposed.

FIG. 2 is an exploded view of the medication delivery pen 10 of FIG. 1. The dose knob/button 22 has a dual purpose and is used both to set the dosage of the medication to be injected and to inject the dosed medicament via the lead-screw 12 and plunger/stopper 14 through the medicament cartridge 16, which is attached to the medication delivery pen 10 through a body 20. In standard medication delivery pens, the dosing and delivery mechanisms are all found within the housing 11 and are not described in greater detail here as they are understood by those knowledgeable of the prior art.

For operation, the medication delivery pen 10 is attached to a pen needle comprising a needle/cannula 30, a septum penetrating cannula 32 and a hub 34. Specifically, a distal movement of the plunger or stopper 14 within the medicament cartridge 16 causes medication to be forced into the needle 30 of the hub 34. The medicament cartridge 16 is sealed by the septum 18, which is punctured by the septum penetrating needle cannula 32 located within the hub 34. The hub 34 is preferably screwed onto the body 20, although other attachment means can be used.

To protect a user from accidental needle sticks, or anyone who handles the pen needle, an outer cover 38, which attaches to the hub 34, covers the hub 34. An inner shield 36 covers the patient needle 30 within the outer cover 38. The inner shield 36 can be secured to the hub 34 to cover the patient needle 30 by any suitable means, such as an interference fit or a snap fit. The outer cover 38 and the inner shield 36 are removed prior to use.

The medicament cartridge 16 is typically a glass tube or vial sealed at one end with the septum 18 and sealed at the other end with the stopper 14. The septum 18 is pierceable by a septum penetrating cannula 32 in the hub 34, but does not move with respect to the medicament cartridge 16. The stopper 14 is axially displaceable within the medicament cartridge 16 while maintaining a fluid tight seal.

Existing medication delivery pens are disclosed in U.S. Patent Application Publication Nos. 2006/0229562 to Marsh et al., which was published on Oct. 12, 2006, and 2007/0149924 to R. Marsh, which was published on Jun. 28, 2007, the entire contents of both of which are hereby incorporated by reference for this purpose.

Medical devices such as medication delivery pens 10 are typically prepared for use by disinfecting the septum 18 with an alcohol swab prior to attaching the pen needle for medication delivery and disinfecting a skin surface at an injection site with an antiseptic wipe prior to administering medicament. However, challenges arise to consistently and accurately disinfect the medication delivery pens 10 and the skin surface for safe patient care. Carrying alcohol swabs and/or antiseptic wipes with the medication delivery pens 10 can be burdensome for a user. Further, the alcohol swabs and/or antiseptic wipes have shelf-life limitations and are typically for single-use only. In certain circumstances, the septum 18 may not be properly disinfected prior to use. Consistently following best disinfection practices is not always practiced and difficult to ensure. Thus, an improved disinfecting device and process for use with medical devices such as medication delivery pens 10 is desired.

SUMMARY OF THE INVENTION

It is an aspect of the present invention to provide a cap that is capable of disinfecting a skin surface at an injection site alone or in combination with disinfecting a medical device or a portion thereof, such as a septum surface. Such a configuration improves workflow and convenience of users using various medical devices such as medication delivery pens, syringes, patch pumps, safety pens and an insulin vial. Poor injection practice is minimized since the user is no longer relied upon to disinfect the skin surface, septum or other exposed surface or portion of the medical device with an alcohol swab or antiseptic wipe. In fact, the cap can be configured to automatically disinfect the septum or other exposed surface or portion, thus saving time. Moreover, the skin surface is more conveniently disinfected either simultaneously or alternately with respect to disinfecting of the septum to improve workflow and optimize time. Disinfecting the medical device and the skin surface with the cap is also more controlled or automated to satisfy high accuracy and performance requirements. Finally, the user no longer needs to carry alcohol swabs and/or antiseptic wipes for the medical device and/or the skin surface.

It is another aspect of the present invention to provide an accessory that is attachable to a device to disinfect the skin surface prior to injection. Such an accessory provides visible light to safely disinfect a skin surface prior to needle injection of the device. The accessory is also adaptable to various products, including medical devices, and is configured to attach and detach for versatile and convenient use.

The foregoing and/or other aspects of the present invention can be achieved by providing a medical device configured to disinfect a skin surface, the device comprising a power source that provides electric power, a light emitting source that uses electric power received from the power source to disinfect the skin surface, and a switch that is configured to be operated by user action, wherein upon activation of the switch, the electric power from the power source is received by the light emitting source to emit visible light and disinfect the skin surface.

The foregoing and/or other aspects of the present invention can further be achieved by providing a cap of a medical device configured to disinfect a skin surface, the cap comprising a power source that provides power to a microcontroller, the microcontroller sensing and controlling the operation of the cap, a light emitting source that emits visible light to disinfect the skin surface under control of the microcontroller, and a switch that causes the microcontroller to activate and deactivate the light emitting source.

The foregoing and/or other aspects of the present invention can also be achieved by providing a method to disinfect a skin surface and inject a medicament using a medical device, the method comprising disposing a light emitting source on an external surface of a cap of the medical device, securing the cap onto the medical device, activating the light emitting source to emit visible light to disinfect the skin surface, exposing the skin surface with the visible light from the light emitting source, removing the cap of the medical device to initiate medication delivery, inserting a needle of the medical device into the skin surface, and injecting the medicament.

The foregoing and/or other aspects of the present invention can additionally be achieved by providing an accessory configured to be attached to a device to disinfect a skin surface, the accessory comprising a light emitting source that emits visible light to disinfect the skin surface, and a mounting mechanism that is configured to attach and detach the light emitting source and the device.

The foregoing and/or other aspects of the present invention can likewise be achieved by providing a method to disinfect a skin surface and inject a medicament using a medical device, the method comprising mounting an accessory to an external surface of a cap of the medical device, the accessory comprising a light emitting source that emits visible light to disinfect the skin surface, activating the light emitting source to disinfect the skin surface, removing the cap of the medical device, inserting a needle of the medical device into the skin surface, and injecting the medicament.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 3:
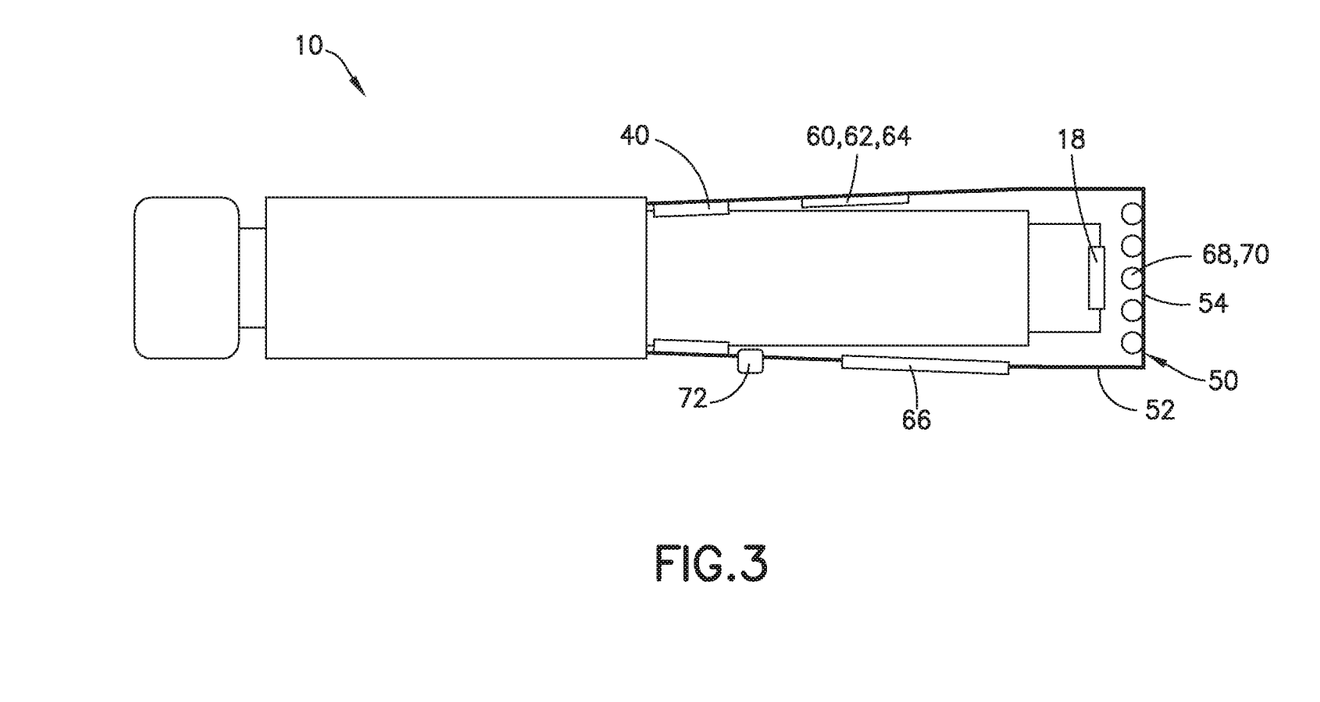
FIG. 3 is a cross-sectional view of an exemplary embodiment of a cap of the medication delivery pen.

FIG. 3 illustrates a cap 50 for a medical device such as a medication delivery pen 10 in accordance with an embodiment of the present invention. The cap 50 includes a sidewall 52 and a top wall 54. The cap 50 is configured to enclose a distal portion of the medication delivery pen 10. Specifically, when the cap 50 is mounted onto the medication delivery pen 10, the top wall 54 is positioned opposing the septum 18 of the medication delivery pen 10. The sidewall 52 is connected to the top wall 54 and encircle the body 20. In this configuration, a distal end of the cap 50 is disposed substantially central in a longitudinal axis of the medication delivery pen 10.

The embodiments of the cap 50 disclosed herein are most commonly configured to mount on to the medication delivery pen 10 without the pen needle present. However, with appropriate modifications, other types of medical devices such as needleless IV connectors, extension sets, IV sets, catheters, syringes (such as pre-Tillable syringes), medication (e.g. insulin) vials, and other devices with externally accessible surfaces such as a septum that require disinfection can incorporate the cap 50 for disinfection purposes. Any surface or portion of the medical device that is contained within the cap 50 and exposed to the electromagnetic radiation source 68 can be disinfected.

With respect to the medication delivery pen 10, the operation of the cap 50 can still take place even if the pen needle is attached to the medication delivery pen 10 and covered by the cap 50. In this scenario, the pen needle can be disinfected rather than the septum 18. However, this condition is typically not preferred because it is not advisable to reuse pen needles.

The cap 50 is configured to be connectable to the medication delivery pen 10 either indirectly via a universal fitting 40 (illustrated in FIGS. 3-5) or directly without the universal fitting 40 (not shown). Exemplary embodiments of the universal fitting 40 include a ring that tightens the fit between a distal end of the cap 50 and the medicament cartridge 16 of the medication delivery pen 10. A rotating sleeve that reduces the inner diameter when rotated and acts similarly to a telescoping pole is another universal fitting 40 that tightens the fit between the cap 50 and the medication delivery pen 10. Further, using ribs, pleats, or scales as the universal fitting 40 provides an expandable, contractible and/or friction surface at the interface between the distal end of the cap 50 and the body 20. The universal fitting 40 can have prongs to provide a mechanical engagement between the cap 50 and the body 20. Finally, another embodiment of the universal fitting 40 is a spring-loaded member that provides an applied force between a distal end of the cap 50 and the medication delivery pen 10.

Figure 4:
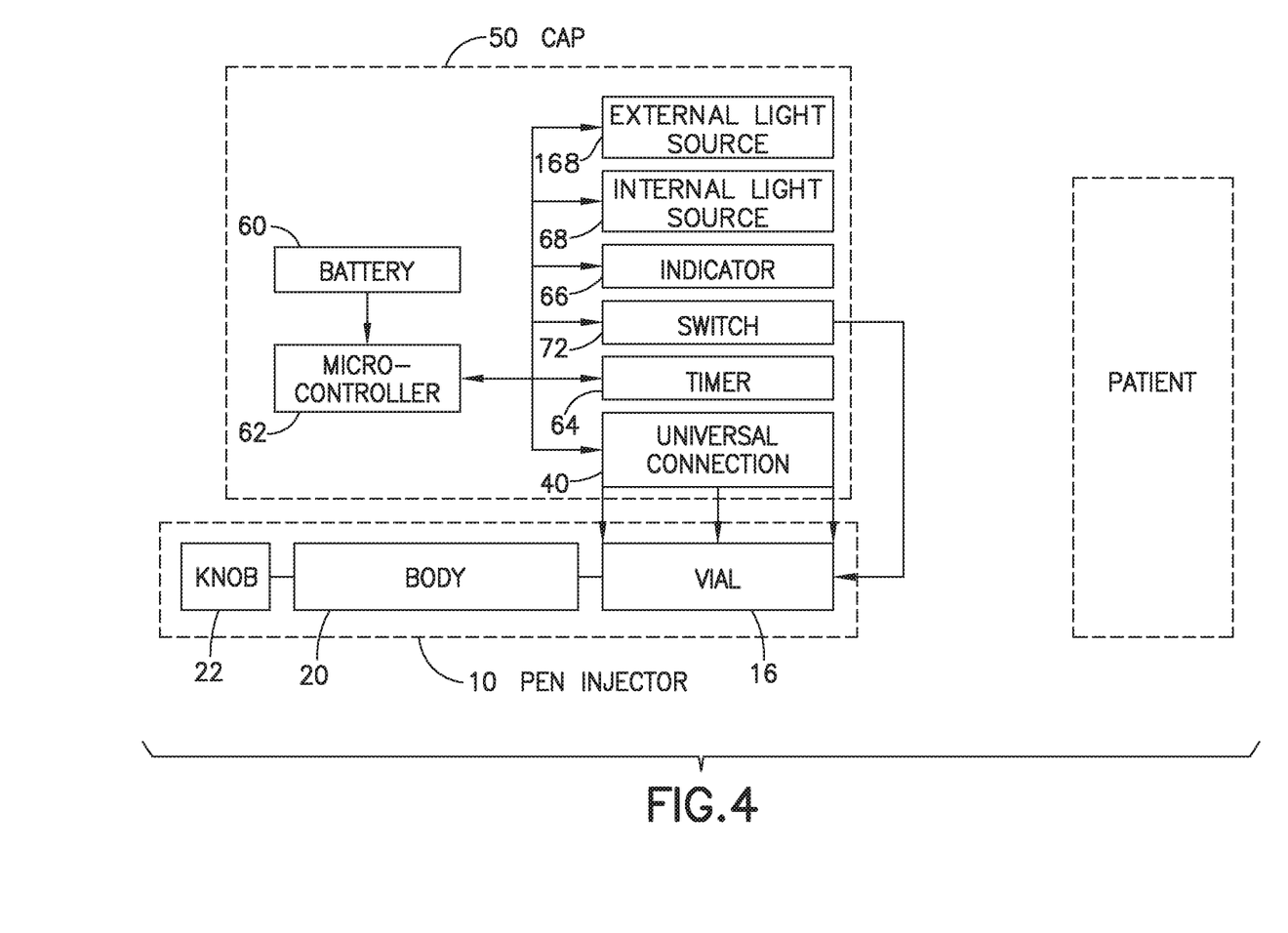
FIG. 4 is a schematic drawing of the electrical components within the cap of FIG. 3 without user input.
Figure 5:
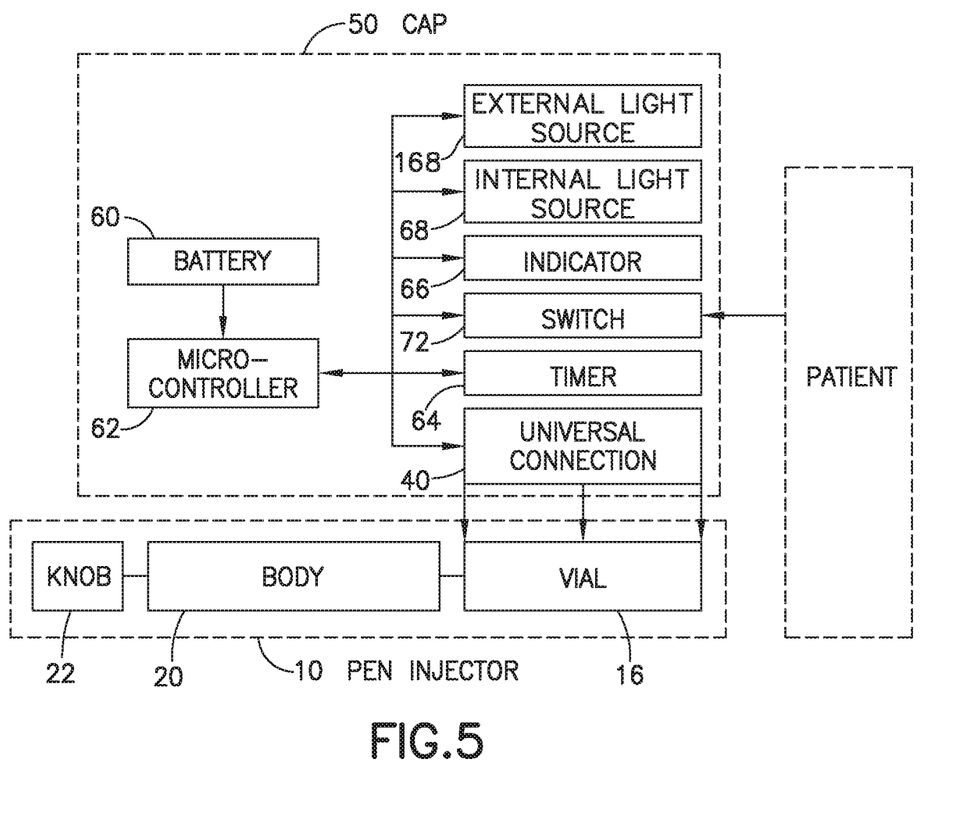
FIG. 5 is a schematic drawing of the electrical components within the cap of FIG. 3 with user input.

Status of the use of the universal fitting 40 is provided as feedback to a microcontroller 62, as described further below and as illustrated in FIGS. 4 and 5. Status of the use of the universal fitting 40 includes, for example, a capped position when an exterior surface of the universal fitting 40 is engaged to an interior surface of the cap 50 and when an interior surface of the universal fitting 40 is engaged to an exterior surface of the medicament cartridge 16 of the medication delivery pen 10. Status of the use of the universal fitting 40 also includes, for example, an uncapped position when one or both of these connections are disengaged. Alternately, the universal fitting 40 can be used without the cooperation of the microcontroller 62 as described further in FIG. 6.

The universal fitting 40 can also cooperate with the microcontroller 62 to vary commands for emitting electromagnetic radiation 70 and/or visible light 170 based on the status. For example, when the universal fitting 40 and the cap 50 are engaged, the microcontroller 62 issues a command for emission of electromagnetic radiation 70 and/or visible light 170. On the other hand, if one or both of the connections are disengaged, the microcontroller 62 does not issue a command for emission of electromagnetic radiation 70 and/or visible light 170.

The cap 50 includes a power source 60 that provides power to the cap 50. The power source 60 is preferably a flexible battery that wraps along an inner surface of the sidewall 52. The power source 60 can also be a lithium battery. Finally, the power source 60 can be wired circuitry that provides power (AC/DC current) to the cap 50.

If the power source 60 is a battery, the battery 60 can be rechargeable via solar energy, motion or electricity (wired or wireless). Alternatively, or in addition, the battery 60 can be discarded and replaced. Further, the cap 50 can be replaced when the battery 60 is depleted. The power source 60 can be disposed on the inner or outer surface of the sidewall 52 or top wall 54.

Figure 6:
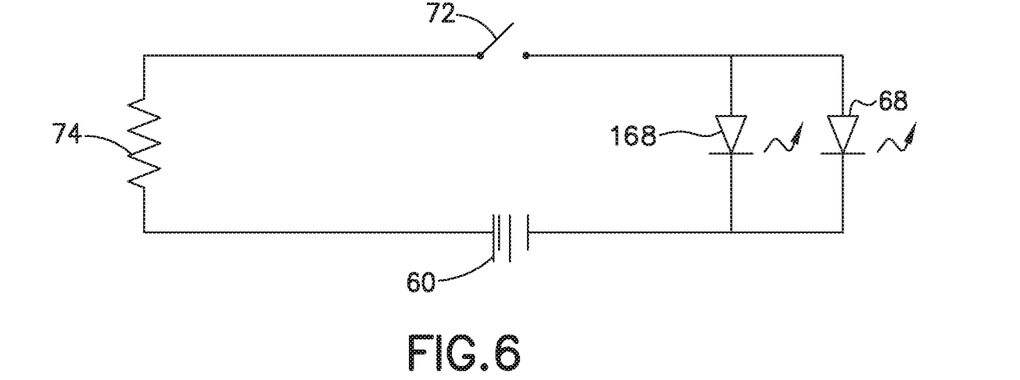
FIG. 6 is a schematic diagram of an electrical circuit of another exemplary embodiment of the cap.

As illustrated in FIGS. 3-5, the power source 60 is configured to specifically provide power to the microcontroller 62 of the cap 50 or directly to an electromagnetic radiation source 68 (see FIG. 6). The electromagnetic radiation source 68 (internal light source) can emit electromagnetic radiation in a selected wavelength range, including ultraviolet (UV) light 70.

In another embodiment, as described below, a light emitting source 168 (external light source) can optionally emit visible light in a selected wavelength range independently and/or uniquely from the electromagnetic radiation source 68. In other words, an embodiment illustrated in FIG. 7 can include both the electromagnetic radiation source 68 and the light emitting source 168 while another embodiment can include only the light emitting source 168. The interrelated operation of the electromagnetic radiation source 68 with the remaining features of the medication delivery pen 10 disclosed herein can be equally configured and applied to the light emitting source 168.

The microcontroller 62, as commonly understood by one skilled in the art, is programmed to sense and control the operation of the cap 50. Specifically, the microcontroller 62 receives feedback and issues commands to various components of the cap 50 including, for example, the universal fitting 40 (as described above), a timer 64, an indicator 66, an electromagnetic radiation source 68, a light emitting source 168, and a switch 72.

The electromagnetic radiation source 68 advantageously emits electromagnetic radiation 70 for disinfection of the septum 18 of the medication delivery pen 10. Electromagnetic radiation 70 is also emitted onto other surface or portion of the medication delivery pen 10 that are enclosed by the cap 50. The electromagnetic radiation source 68 is disposed on an inner surface of the top wall 54 of the cap 50.

Figure 7:
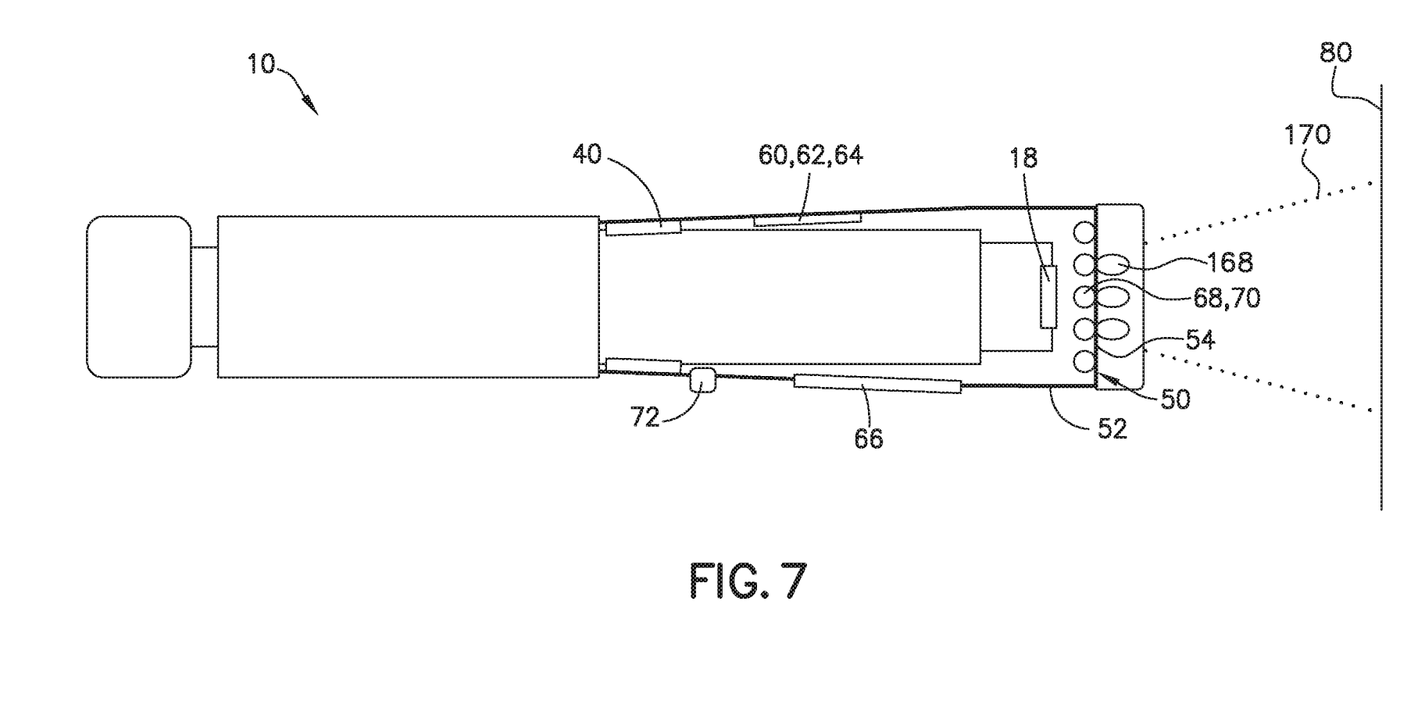
FIG. 7 is a cross-sectional view of an exemplary embodiment of a cap of the medication delivery pen of FIG. 3 with a light emitting source on an external surface of the cap.

In another embodiment, the light emitting source 168 advantageously emits visible light 170 for disinfection of the skin surface 80 at the injection site prior to needle insertion. The visible light 170 can also be applied to other medical devices and surfaces. However, such an application will not be as effective as ultraviolet light emitted by the electromagnetic radiation source 68 when disinfecting.

The light emitting source 168 is disposed on an external surface of the top wall 54 of the cap 50 as illustrated in FIG. 7 to emit visible light 170 to disinfect the skin surface 80. However, the light emitting source 168 can also be disposed on the external surface of the side wall 52 of the cap 50, on a longitudinal side surface of the housing 11 of the medication delivery pen 10, or on any other external surface of any other medical device 10.

In yet another embodiment, the power source 60 and the electromagnetic radiation source 68 are both stacked on the inner surface of the top wall 54 of the cap 50. Accordingly, the electromagnetic radiation source 68 is disposed distal to the power source 60 so that the electromagnetic radiation 70 can be directly emitted on the septum 18 of the medication delivery pen 10, as well as onto other surface or portion of the medication delivery pen 10.

In a further embodiment, the electromagnetic radiation source 68 is positioned so that the electromagnetic radiation 70 are not directly emitted on the septum 18. Although radiating electromagnetic radiation 70 directly on the septum 18 is more efficient, such a configuration is not critical for effective operation and disinfecting.

The command that controls the operation of the electromagnetic radiation source 68 and the light emitting source 168 is received from the microcontroller 62 or directly from the switch 72 (see FIG. 6). The electromagnetic radiation source 68 and the light emitting source 168 are preferably a commercially known and available plurality of light emitting diodes (LEDs). LEDs provide advantages in emitting light in optimal wavelength(s) for improved disinfection, have a small footprint, and consume far less energy due to their instant on/off capability. Nevertheless, any energy source that disinfects can be used.

A variety of wavelength ranges from the electromagnetic spectrum can be used for disinfection. As an example, the relative effectiveness of UV light wavelengths for this process is known as the germicidal action spectrum, which peaks at a maximum wavelength 265 nm (UV-C). Thus, a preferred wavelength range of UV light 70 is between 250 nm and 280 nm. The necessary exposure for many applications ranges between 10 mJ/cm$^2$ and 100 mJ/cm$^2$.

In view of the above, alternative wavelengths may be used. All UV light wavelengths shorter than 300 nm are effective to disinfect and kill microorganisms. The main principle of operation is based on Ultra-Violet Germicidal Irradiation (UVGI). This disinfection method uses short wavelength ultraviolet light to kill or inactivate microorganisms by destroying nucleic acids and disrupting or causing photo-degradation of their DNA. Accordingly, this disinfection method can be harmful to humans and inorganic materials such that exposure to these wavelengths can severely damage skin and eyes, for example.

UVGI is often used to sterilize equipment such as safety goggles, instruments, pipettes, and other devices. Lab personnel also sterilize glassware and plastic-ware in this way. Microbiology laboratories use UVGI to sterilize surfaces inside biological safety cabinets ("hoods") between uses. Thus, UV disinfection is best conducted when humans and inorganic materials are not present. However, the limitations of UV disinfection reduces its usefulness in certain situations.

Given enough energy and time, longer wavelengths can also be equally as effective. However, disinfection at each location should be managed separately to achieve optimal results. White light is understood as the mixture of all of the wavelengths in the visible spectrum. Visible light is understood to generally be in the range of 400-700 nm. Light in the wavelength range of 400-410 nm, also known as violet light, specifically has disinfection capabilities on bacteria cells, but without the same impact that UV light has on mammalian cells. This visible light application can preferably be a mixed-wavelength application, although a monochromatic light is also possible. Human cells can be exposed to visible light without the danger to human cells and the loss of cellular viability. For example, it has been shown in the literature that visible light kill gram negative and gram positive bacteria, bacterial endospores, yeast, mold, and fungi. This is because mammal and bacteria cells both have porphyrin molecules, but mammalian cells have more sophisticated methods for coping with oxidative damage compared to bacteria cells, making bacteria cells more primitive and not as resistant to visible light.

The destruction of microorganisms by UV light 70 is an exponential process. The higher the given exposure, the higher the proportion of microorganisms destroyed. Consequently, the exposure necessary to destroy 99% is double the value to destroy 90%. It follows therefore that the exposure required to kill 99.9% is three times the value to destroy 90% and the exposure required to kill 99.99% is four times the value to destroy 90%.

Although a preferred wavelength range of UV light 70 and visible light 170 is desired, the duration of emission of UV light 70 and visible light 170 required for disinfection is a function of distance, power, time and wavelength. The required exposure (i.e. UV Dose, visible light dose or Energy) can be calculated using the following equation:

$$\text{Light dose (J/m2)} = \text{Irradiance (W/m2)} \times \text{Exposure Time (seconds)}$$

The necessary wavelength and exposure time can be calculated based on a required dose of UV light 70 as set forth in the following table:

| Bacteria-UV Light Dose Correlation Table | | | | |
|---|---|---|---|---|
| | UV light exposure (dose) in J/m2 required to achieve 90%-99.99% reduction of the specified microorganism types | | | |
| Microorganism (microbe) | 90% (1 log) | 99% (2 log) | 99.9% (3 log) | 99.99% (4 log) |
| *Bacillus anthracis* - Anthrax | 45.2 | 90.40 | 135.60 | 180.80 |
| *Bacillus anthracis* spores - Anthrax spores | 243.2 | 486.40 | 729.60 | 972.80 |
| *Bacillus magaterium* sp. (spores) | 27.3 | 54.60 | 81.90 | 109.20 |
| *Bacillus magaterium* sp. (veg.) | 13.0 | 26.0 | 39.0 | 52.0 |
| *Bacillus paratyphusus* | 32.0 | 64.0 | 96.0 | 128.0 |
| *Bacillus subtilis* spores | 116.0 | 232.0 | 348.0 | 464.0 |
| *Bacillus subtilis* | 58.0 | 116.0 | 174.0 | 232.0 |
| *Clostridium difficile* (*C. difficile* or *C. diff*) | 60.0 | 120.0 | 180.0 | 240.0 |
| *Clostridium tetani* | 130.0 | 260.0 | 390.0 | 520.0 |
| *Corynebacterium diphtheria* | 33.7 | 67.4 | 101.1 | 134.80 |
| *Ebertelia typhosa* | 21.4 | 42.80 | 64.2 | 85.60 |
| *Escherichia coli* | 30.0 | 60.0 | 90.0 | 120.0 |
| *Leptospira canicola* - infectious Jaundice | 31.5 | 63.0 | 94.5 | 126.0 |
| *Micrococcus candidus* | 60.5 | 121.0 | 181.5 | 242.0 |
| *Micrococcus sphaeroides* | 10.0 | 20.0 | 30.0 | 40.0 |
| MRSA | 32.0 | 64.0 | 96.0 | 128.0 |
| *Mycobacterium tuberculosis* | 62.0 | 124.0 | 186.0 | 248.0 |
| *Neisseria catarrhalis* | 44.0 | 88.0 | 132.0 | 176.0 |
| *Phytomonas tumefaciens* | 44.0 | 88.0 | 132.0 | 176.0 |
| *Proteus vulgaris* | 30.0 | 60.0 | 90.0 | 120.0 |
| *Pseudomonas aeruginosa* | 55.0 | 110.0 | 165.0 | 220.0 |
| *Pseudomonas fluorescens* | 35.0 | 70.0 | 105.0 | 140.0 |
| *Salmonella enteritidis* | 40.0 | 80.0 | 120.0 | 160.0 |
| *Salmonela paratyphi* - Enteric fever | 32.0 | 64.0 | 96.0 | 128.0 |
| *Salmonella typhosa* - Typhoid fever | 21.5 | 43.0 | 64.5 | 86.0 |
| *Salmonella typhimurium* | 80.0 | 160.0 | 240.0 | 320.0 |
| *Sarcina lutea* | 197.0 | 394.0 | 591.0 | 788.0 |
| *Serratia marcescens* | 24.2 | 48.4 | 72.6 | 96.8 |
| *Shigella dyseteriae* - Dysentery | 22.0 | 44.0 | 66.0 | 88.0 |
| *Shigella flexneri* - Dysentery | 17.0 | 34.0 | 51.0 | 68.0 |
| *Shigella paradysenteriae* | 16.8 | 33.6 | 50.4 | 67.2 |
| *Spirillum rubrum* | 44.0 | 88.0 | 132.0 | 176.0 |
| *Staphylococcus albus* | 18.4 | 36.8 | 55.2 | 73.6 |
| *Staphylococcus aureus* | 26.0 | 52.0 | 78.0 | 104.0 |
| *Staphylococcus hemolyticus* | 21.6 | 43.2 | 64.8 | 86.4 |
| *Staphylococcus lactis* | 61.5 | 123.0 | 184.5 | 246.0 |

-continued

Bacteria-UV Light Dose Correlation Table

| Microorganism (microbe) | UV light exposure (dose) in J/m2 required to achieve 90%-99.99% reduction of the specified microorganism types | | | |
|---|---|---|---|---|
| | 90% (1 log) | 99% (2 log) | 99.9% (3 log) | 99.99% (4 log) |
| *Streptococcus viridans* | 20.0 | 40.0 | 60.0 | 80.0 |
| *Vibrio* comma - *Cholera* | 33.75 | 67.5 | 101.25 | 135.0 |

Alternatively, energy consumption can be calculated using a targeted wavelength through the equation below:

$$E = hc/\lambda \text{ joules}$$

Where:
h=Planck's constant ($6.626 \times 10^{-34}$ J s)
c=Speed of light ($2.998 \times 10^8$ m s$^{-1}$)
λ=Wavelength in m Once the target energy is identified, the energy consumption (i.e. power) can be calculated using the following equation:

$$P = \frac{\Delta E}{\Delta t}$$

When the power P (in watts) is calculated, an appropriate power source 60 can be selected to provide the required energy for the desired duration. For example, assuming a 10 second exposure (based on patient comfort) to 100 mJ/cm² (per the necessary exposure to disinfect for UV) over an area the size of a pen cap (approximately 3.14 cm²), approximately 0.0314 Watts of energy is required. Given that the visible (violet) light has a longer wavelength, under the same conditions, it would consume more energy. This analysis indicates that a basic button battery or a similar small power source is feasible to operate UV light and visible light for multiple exposures for the life of the battery. The amount of time required to disinfect is related to the distance from the light source, the light dose, wavelength and microorganism.

The cap 50 further includes the switch 72 that causes the microcontroller 62 to generate commands that activate and deactivate the electromagnetic radiation source 68 and the light emitting source 168. Alternately, as illustrated in FIG. 6, the switch 72 itself connects and disconnects the power source 60 to the electromagnetic radiation source 68 and the light emitting source 168 to control illumination of the electromagnetic radiation source 68. As illustrated in FIG. 3, the switch 72 is disposed on the inner surface of the sidewall 52 of the cap 50. However, the switch 72 can be disposed on any inner or outer surface of the cap 50. The switch 72 can be an actuated switch such as a micro switch, a spring-loaded switch, or a button switch. In another embodiment, the switch 72 includes a first and second switch to separately activate and deactivate the electromagnetic radiation source 68 and the light emitting source 168, respectively.

Specifically, the micro switch and/or the spring-loaded switch can be activated based on pressure from the user prior to injection (manual) or an exerted force between the cap 50 and the medication delivery pen 10 during assembly (automatic). As illustrated in FIG. 4, upon sensing an increased pressure, the micro switch 72 sends a signal to the microcontroller 62 to activate the electromagnetic radiation source 68 and the light emitting source 168 (capped, pressed position). When the user releases the pressure or when the cap 50 and the medication delivery pen 10 are disassembled, the pressure is lessened and the micro switch 72 sends a signal to the microcontroller 62 to deactivate the electromagnetic radiation source 68 and the light emitting source 168 (uncapped, relaxed position).

The spring force therefore provides a one-time activation of the electromagnetic radiation source 68 and the light emitting source 168. After a predetermined time period, the electromagnetic radiation source 68 and the light emitting source 168 are deactivated. Alternatively, a manual switch could be implemented to trigger the activation of the electromagnetic radiation source 68 and the light emitting source 168 for a desired duration prior to each use. The activation and deactivation of the electromagnetic radiation source 68 and the light emitting source 168 in this regard can be automatic, instantaneous, simultaneous or alternate based on the programmed signaling from the microcontroller 62 or the engagement and disengagement of the micro switch 72.

The switch 72, if provided as a spring-loaded switch, can release a spring force upon receiving an increased pressure during assembly of the cap 50 to the medication delivery pen 10. The spring force provides a one-time activation of the electromagnetic radiation source 68 and the light emitting source 168. After a predetermined period of time, the electromagnetic radiation source 68 and the light emitting source 168 is deactivated.

The timer 64 can be incorporated into the spring-loaded switch 72, for example, to provide a predetermined time period of electromagnetic radiation emission and visible light emission or a time delay before beginning electromagnetic radiation emission and visible light emission. The timer 64 can be activated when the switch 72 is engaged. For example, the timer 64 can cause the electromagnetic radiation source 68 to emit electromagnetic radiation 70 at a wavelength of 265 nm for up to 120 seconds when the distance between the electromagnetic radiation source 68 and the septum 18 of the medication delivery pen 10 is two inches. In a similar manner, the timer 64 can cause the light emitting source 168 to emit visible light 170 at a wavelength of 405 nm for a specific amount of time at a specific distance between the light source 168 and the skin surface 80. The timer 64 can also cooperate with the microcontroller 62 to vary commands for activating and deactivating the electromagnetic radiation source 68 and the light emitting source 168.

As illustrated in FIG. 5, the switch 72, when provided as a button switch, can deflect, release a force and/or establish electrical contact with the microcontroller 62 based on an operation, such as a depression, for example, by a user such as the clinician or patient. In this manner, the user is able to control the activation and deactivation of the electromagnetic radiation source 68 and the light emitting source 168.

The switch 72 can also be a proximity sensor, a Hall Effect sensor, a photo sensor, an optical sensor and a force sensor. The operation of these sensors are commonly understood by one skilled in the art. The proximity sensor can sense that the cap 50 is disposed on the medication delivery pen 10 and instruct the microcontroller 62 of this condition. Subsequently, the microcontroller 62 can command the electromagnetic radiation source 68 to emit electromagnetic radiation 70 and command the light emitting source 168 to emit visible light 170. When the cap 50 is removed from the medication delivery pen 10, the proximity sensor informs the microcontroller 62 of this condition and the microcontroller commands the electromagnetic radiation source 68 to stop emitting electromagnetic radiation 70 and commands the light emitting source 168 to stop emitting visible light 170.

The cap 50 further includes an indicator 66 that displays a plurality of conditions such as indicating when the electromagnetic radiation source 68 is activated or deactivated, when the light emitting source 168 is activated or deactivated, when the disinfecting/sterilizing process of the medical device 10 or skin surface 80 is complete, and the remaining life of the power source 60. The indicator 66 communicates with the microcontroller 62 to receive a status of one or more of these conditions prior to display. The indicator 66 displays these conditions via a plurality of media commonly known by those skilled in the art such as, for example, colors, symbols and text.

The cap 50 described above provides advantages not realized in the prior art. The cap 50 improves the workflow and convenience of users, such as clinicians or patients, using medication delivery pens 10. Specifically, the user no longer needs to clean the skin surface 80, the septum 18, or other surfaces or portions of the medical device, such as the medication delivery pen 10, with an alcohol swab or an antiseptic wipe. This is because the cap 50 alone can disinfect the skin surface 80, the septum 18 and other surfaces or portions of the medication delivery pen 10 using electromagnetic radiation 70 and visible light 170. Accordingly, the user does not need to carry a separate alcohol swab package or antiseptic wipes with the medication delivery pen 10 and does not need to manage extra steps in the process for disinfecting the skin surface 80, the septum 18 or other surface or portion. Also, the skin surface 80, the septum 18 and other surface or portion are disinfected more reliably without user error such as ineffective disinfecting or failure to disinfect.

To operate the cap 50 with the medication delivery pen 10, the user simply attaches the cap 50 to the medication delivery pen 10 with or without the universal fitting 40 as described above. Then, either automatically or manually by the user, the electromagnetic radiation source 68 and the light emitting source 168 are activated. The electromagnetic radiation source 68 emits electromagnetic radiation 70 on the exposed septum 18 of the medication delivery pen 10 to disinfect the septum 18. Other surface or portion of the medication delivery pen 10 is also disinfected. The light emitting source 168 emits visible light 170 to the skin surface 80 prior to needle insertion. After the disinfection is complete, the cap 50 is subsequently removed. Next, the pen needle is attached to the medicament cartridge 16 of the medication delivery pen 10. The medication delivery pen 10 is now ready for medication delivery into the disinfected skin surface 80. A needle of the pen needle is subsequently inserted into the skin surface 80 to dispense medicament to the patient.

Upon completion of medication delivery, the pen needle is to be removed from the medicament cartridge 16 and discarded. The septum 18 of the medicament cartridge 16 in the medication delivery pen 10 is now exposed. Next, the user returns and attaches the cap 50 to the medication delivery pen 10. Disinfection of the septum 18 and other surface or portion of the medication delivery pen 10 resumes similarly as described above. If another dose of medicament is to be dispensed, another skin surface 80 can also be disinfected by the light emitting source 168 in a similar manner as described above. This disinfection process can be repeated between multiple injections of the medication delivery pen 10.

In a simpler implementation as mentioned above and illustrated in FIG. 6, the button switch 72 and a current limiting resistor 74 can control the electric power from the power source 60 directly to the electromagnetic radiation source 68 and to the light emitting source 168, without the microcontroller 62. In this case, the user controls the duration of the disinfection by the length of time that the button switch 72 is operated, activated or depressed, for example. That is, when the switch 72 is in operation, or depressed, the electromagnetic radiation source 68 and the light emitting source 168 use the electric power from the power source 60 to illuminate the electromagnetic radiation source 68 and the light emitting source 168. When the switch 72 is not in operation, or not depressed, the electromagnetic radiation source 68 and the light emitting source 168 do not use the electric power from the power source 60. As a result, no disinfection takes place.

As described above, FIG. 7 illustrates the embodiment of the medication delivery pen 10 covered by the cap 50 which includes the electromagnetic radiation source 68 and the light emitting source 168 to disinfect the septum 18 of the medication delivery pen 10 and the skin surface 80, respectively. The features of the embodiments above can be equally applied to this embodiment as long as the operation of the features does not contradict the operation of this embodiment.

This embodiment advantageously allows for disinfection as frequently as the power source allows. As described above with respect to the feasibility study, a basic button battery or similar small power source can operate the electromagnetic radiation source 68 and the light emitting source 168 for multiple exposures for the life of the battery. Such a configuration provides minimal limitations on shelf life and potency because of its long term use.

Additionally, the dual disinfection technology disclosed in this embodiment saves time and improves the workflow and convenience of users, such as clinicians or patients, using medication delivery pens 10. Another advantage is that the user no longer has to rely on an alcohol swab or an antiseptic wipe to disinfect the skin surface 80, the septum 18 or other exposed surfaces or portions of the medication delivery pen 10. In fact, the cap 50 can be configured to automatically disinfect the septum 18 or other exposed surface or portion of the medication delivery pen 10, thus saving time. Moreover, the skin surface 80 is more conveniently disinfected either simultaneously or alternately with respect to disinfecting of the septum 18 to improve workflow and optimize time. Disinfecting the medication delivery pen 10 with the cap 50 is also advantageously more controlled or automated to satisfy high accuracy and performance requirements. Finally, the user no longer needs to carry alcohol swabs and/or antiseptic wipes for the medical device and/or the skin surface 80. As a result, the disclosed embodiment provides a solution to medication delivery pen 10 for safe skin disinfection using light within the visible light spectrum.

Figure 8:
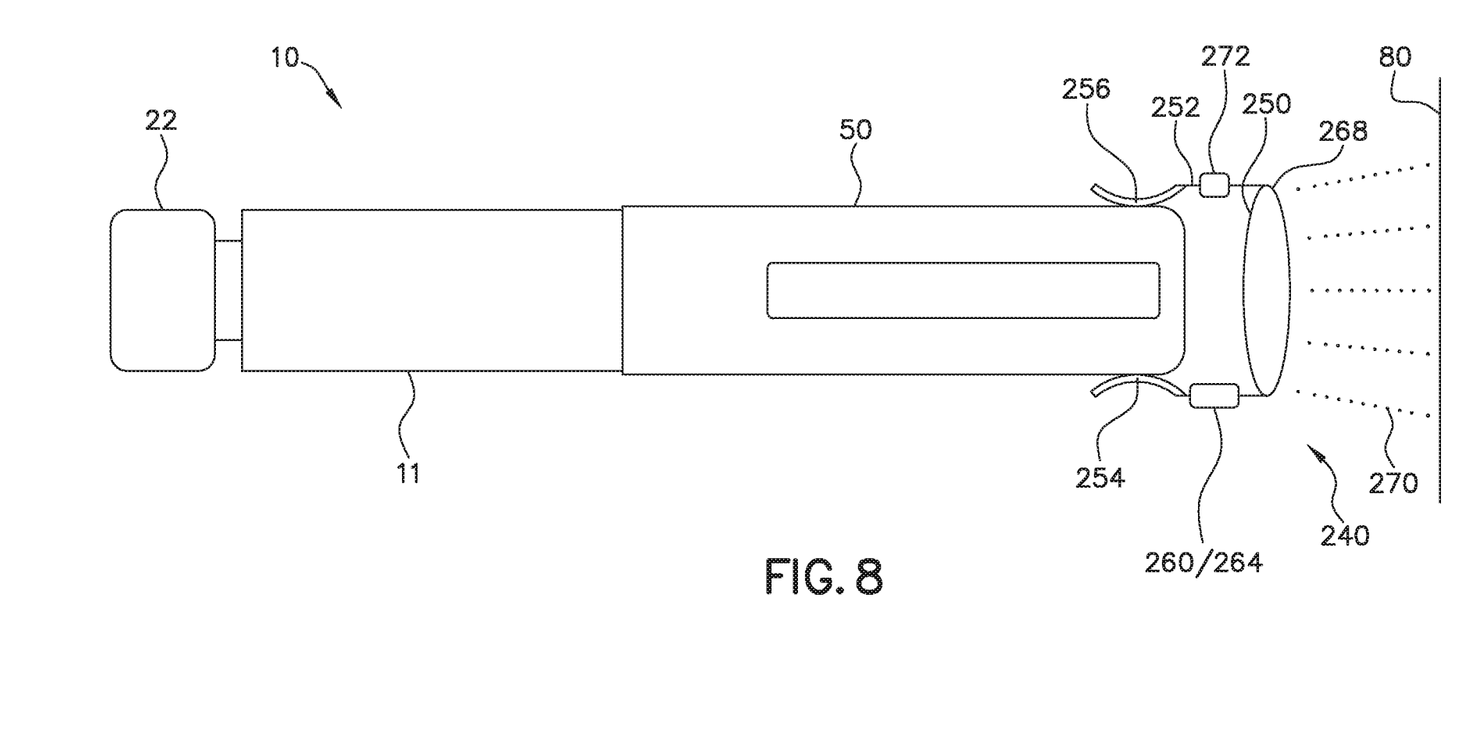
FIG. 8 is a cross-sectional view of an exemplary embodiment of an accessory attached to a medication delivery pen used to disinfect a skin surface.

FIG. 8 illustrates another embodiment providing an accessory 240 that is configured to mount onto a medication delivery pen 10 to disinfect the skin surface 80 at the injection site. The features of the embodiments above can be equally applied to this embodiment as long as the operation of these features does not contradict the operation of this embodiment. Specifically, the accessory 240 can be used with any device including any of the medical devices 10 identified above, as well as a syringe with or without a syringe shield and a medication delivery pen with or without a cap. At least a power source 260, a timer 264, a light emitting source 268 and a switch 272 disclosed in this embodiment are the same or similar to the corresponding components in the embodiments described above.

Instead of the light emitting source 268 being integral to the medication delivery pen 10 as described in embodiments above, this embodiment provides a light emitting source 268 via the accessory 240 that connects to the medication delivery pen 10. The accessory 240 is attachable and detachable to the medication delivery pen 10, such as a medication delivery pen 10, as illustrated in FIG. 8. Specifically, the cap 50 of the medication delivery pen 10 is configured to engage the accessory 240.

In one embodiment, the accessory 240 includes an optional container 250 that carries the light emitting source 268. The container 250 is a cylindrical cavity sized to store and retain the light emitting source 268. The light emitting source 268 is retained in the container 250 via adhesive, for example, although other means of retention are contemplated.

The accessory 240 further includes a mounting mechanism 252 that attaches the accessory to the medication delivery pen 10. FIG. 8 illustrates the mounting mechanism 252 as comprising a mechanical clip. However, other exemplary mounting mechanisms 252 can include a universal cap similar to the universal fitting described above, a spring loaded locking mechanism, a press fit, adhesion, hook and loop fasteners (Velcro), a threaded member, a spring clip and a button, for example. The mounting mechanism 252 is advantageously selected based on the specific device 10 being used.

The mechanical clip 252 elastically compresses the cap 50 of the medication delivery pen 10 to secure the accessory onto the medication delivery pen 10. In one embodiment, a proximal end portion of the mechanical clip 252 includes electrical contacts 254 that engage electrical contacts 256 of the medication delivery pen 10 at the compressed section. In this manner, electrical power is transmitted from the power source 60, through the electrical contacts 254, 256 and through electrical wiring disposed in the hollow mechanical clip 252 to electrically connect to and provide energy to the power source 260.

In another embodiment, the power source 260 is an independent, stand-alone battery such as a battery commonly used for a watch or a rechargeable battery. Accordingly, the power source 260 provides electrical energy to the timer 264, light emitting source 268 and switch 272. In a further embodiment, the accessory 240 is configured to attach to the medication delivery pen 10 comprising the cap 50 with the electromagnetic radiation source 68 as similarly described in previous embodiments.

The embodiments of the accessory 240 disclosed in FIG. 8 advantageously provide visible light 270 to safely disinfect a skin application surface 80 for medical product use. The accessory 240 is advantageously adaptable to various medical devices 10 and is configured to attach and detach for versatile and convenient use. The accessory 240 can also advantageously be attached and detached to non-medical devices 10 for convenient use, such as an accessory to a phone or a purse. Finally, the accessory 240 provides also similar advantages as described above.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A cap of a medical device configured to disinfect a skin surface, the cap comprising:
   a power source that provides electric power;
   a light emitting source that uses electric power received from the power source to disinfect the skin surface, the light emitting source being disposed on an external surface of the cap;
   a switch that is configured to be operated by user action; and
   an electromagnetic radiation source disposed inside the cap to emit UV light, wherein
   upon activation of the switch, the electric power from the power source is received by the light emitting source to emit visible light to disinfect the skin surface, the electric power from the power source is received by the electromagnetic radiation source to emit UV light to disinfect the medical device or a portion thereof; and
   the medical device includes one of a medication delivery pen and a syringe.

2. The cap of claim 1, wherein the power source comprises a battery.

3. The cap of claim 1, wherein
   the electromagnetic radiation source emits light in a bandwidth to disinfect the portion of the medical device;

the light emitting source emits light in a bandwidth different from the light emitted from the electromagnetic radiation source; and the portion of the medical device is a surface of the medical device.

4. A medication pen needle assembly, comprising:
the cap of claim 1; wherein
the electric power from the power source is applied to the electromagnetic radiation source to radiate electromagnetic radiation on a needle.

5. The cap of claim 1, wherein the light emitting source emits visible light in a wavelength range between 400 nm and 410 nm.

6. The cap of claim 1, wherein the light emitting source operates simultaneously with the electromagnetic radiation source.

7. The cap of claim 1, wherein the light emitting source operates alternately with respect to the electromagnetic radiation source.

8. The cap of claim 1, wherein a wavelength of the emission from the light emitting source is different from a wavelength of the UV light emitted from the electromagnetic radiation source.

9. A medication pen needle assembly, comprising:
the cap of claim 1; and
a universal fitting disposed between the cap and the medical device to secure the cap onto the medical device.

10. A cap of a medical device configured to disinfect a skin surface, the cap comprising:
a power source that provides power to a microcontroller, the microcontroller sensing and controlling the operation of the cap;
a light emitting source that emits visible light to disinfect the skin surface under control of the microcontroller, the light emitting source being disposed on an external surface of the cap;
an electromagnetic radiation source disposed inside the cap to emit UV light to disinfect the medical device or a portion thereof under control of the microcontroller; and
a switch that causes the microcontroller to activate and deactivate the light emitting source and the electromagnetic radiation source; wherein
the medical device includes one of a medication delivery pen and a syringe.

11. The cap of claim 10, wherein the switch comprises a micro switch, a proximity sensor, a Hall effect sensor, a photosensor, an optical sensor or a force sensor.

12. The cap of claim 10, further comprising an indicator that indicates at least one of whether the electromagnetic radiation source is activated, whether the light emitting source is activated, whether either disinfection process is complete, and a remaining life of the power source.

13. The cap of claim 10, further comprising a timer that controls at least one of a time delay, a duration of the radiation and a duration of the visible light emitted.

14. A method for disinfecting a skin surface and injecting a medicament using a medical device, the method comprising:
disposing a light emitting source on an external surface of a cap of the medical device, the medical device including one of a medication delivery pen and a syringe;
disposing an electromagnetic radiation source on an internal surface of the cap of the medical device;
securing the cap onto the medical device;
activating the light emitting source via a power source to emit visible light to disinfect the skin surface;
exposing the skin surface with the visible light from the light emitting source;
activating the electromagnetic radiation source via the power source to emit UV light to disinfect the medical device or a portion thereof;
exposing the medical device or the portion thereof with the UV light from the electromagnetic radiation source;
removing the cap of the medical device to initiate medication delivery;
inserting a needle of the medical device into the skin surface; and
injecting the medicament.

15. The method of claim 14, further comprising
securing the cap onto the medical device; wherein
the electromagnetic radiation source is automatically activated.

16. The method of claim 15, further comprising removing a pen needle from the medical device to expose a septum of the medical device prior to securing the cap.

17. The method of claim 14, wherein the electromagnetic radiation source emits ultraviolet light in a bandwidth between 250 nm and 280 nm to disinfect the medical device or portion thereof.

18. An accessory configured to be attached to a device to disinfect a skin surface, the accessory comprising:
a light emitting source that emits visible light to disinfect the skin surface; and
a mounting mechanism that is configured to attach and detach the light emitting source and the device, the mounting mechanism including electrical contacts to transmit electrical power from a power source to the light emitting source; wherein
the device includes one of a medication delivery pen having a pen cap and a syringe having a syringe shield;
the device includes an electromagnetic radiation source that emits UV light to disinfect the device or a portion thereof; and
the mounting mechanism is attached to one of the pen cap and the syringe shield.

19. The accessory of claim 18, wherein the mounting mechanism comprises one of a universal cap, spring loaded member, press fit, adhesive, threads and a button.

20. The accessory of claim 18, further comprising
a switch to activate and deactivate the light emitting source and the electromagnetic radiation source.

21. The accessory of claim 18, further comprising a container to carry the light emitting source.

22. An assembly configured to disinfect a skin surface and a medical device or portion thereof, the assembly comprising:
a cap of the medical device comprising:
a power source that provides electric power;
an electromagnetic radiation source uses the electric power received from the power source to emit electromagnetic radiation for disinfection; and
a switch that is configured to be operated by user action; and
the accessory of claim 18 wherein
the mounting mechanism attaches onto an external surface of the cap; and
upon activation of the switch, the electric power from the power source is applied to at least one of the electromagnetic radiation source and the light emitting source to disinfect.

23. The assembly of claim 22, wherein
the cap of the medical device comprises electrical contacts; and
the electrical contacts of the mounting mechanism engage the electrical contacts of the cap to supply power from the power source to the light emitting source.

24. A method for disinfecting a skin surface and injecting a medicament using a medical device, the method comprising:
disposing an electromagnetic radiation source on an internal surface of a cap of the medical device;
mounting an accessory to an external surface of the cap of the medical device via a mounting mechanism, the mounting mechanism including electrical contacts to transmit electrical power from a power source to a light emitting source, the accessory comprising the light emitting source to emits visible light for disinfecting the skin surface;
activating the light emitting source to disinfect the skin surface;
activating the electromagnetic radiation source to emit UV light to disinfect the medical device or a portion thereof;
removing the cap of the medical device, the medical device including one of a medication delivery pen having a pen cap and a syringe having a syringe shield;
inserting a needle of the medical device into the skin surface; and
injecting the medicament.

25. The method of claim 24, further comprising:
securing the cap onto the medical device;
establishing electrical communication between the cap and the accessory.

* * * * *